United States Patent
MacDougall et al.

(10) Patent No.: US 10,426,379 B2
(45) Date of Patent: Oct. 1, 2019

(54) VESTIBULAR TESTING APPARATUS

(71) Applicant: Natus Medical Incorporated, San Carlos, CA (US)

(72) Inventors: Hamish MacDougall, Sydney (AU); Robert Nygren, Schaumburg, IL (US); Wendy Crumley-Welsh, Schaumburg, IL (US)

(73) Assignee: Natus Medical Incorporated, Pleasanton, CA (US)

( * ) Notice: Subject to any disclaimer, the term of this patent is extended or adjusted under 35 U.S.C. 154(b) by 0 days.

(21) Appl. No.: 14/686,311

(22) Filed: Apr. 14, 2015

(65) Prior Publication Data

US 2016/0287143 A1    Oct. 6, 2016

(30) Foreign Application Priority Data

Mar. 30, 2015  (DK) .................................. 2015 70187
Mar. 30, 2015  (EP) ..................................... 15161784

(51) Int. Cl.
*A61B 5/11*    (2006.01)
*A61B 5/00*    (2006.01)
(Continued)

(52) U.S. Cl.
CPC ........... *A61B 5/1128* (2013.01); *A61B 5/1114* (2013.01); *A61B 5/7275* (2013.01);
(Continued)

(58) Field of Classification Search
CPC .................................................... A61B 5/1128
(Continued)

(56) References Cited

U.S. PATENT DOCUMENTS 5,967,968 A * 10/1999 Nishioka ............... G01B 9/04
                                                              600/104
6,568,396 B1 * 5/2003 Anthony ................ A61B 5/11
                                                              128/897
(Continued)

FOREIGN PATENT DOCUMENTS

EP     2 946 720 A1    11/2015
JP     2005-192925 A    7/2005
(Continued)

OTHER PUBLICATIONS

Wikipedia, Rotation matrix, Retrieved Mar. 26, 2015.*
(Continued)

*Primary Examiner* — Gary Jackson
*Assistant Examiner* — Jonathan Kuo
(74) *Attorney, Agent, or Firm* — Temmerman Law; Mathew J. Temmerman

(57) ABSTRACT

A system for detecting and recording head orientations of a person includes: a first sensor device capable of providing sensor data regarding a head orientation of a person in a three-dimensional space; a medical data acquisition system configured for storing and outputting the sensor data from the first sensor device; and a processor configured for processing the sensor data from the medical data acquisition system, outputting a first signal representing the head orientation, and generating an image for presentation by a graphical display; wherein the image comprises: a first reference indicator; an orientation indicator, wherein a position of the orientation indicator in the image is determined based on the first signal from the processor, and a feedback indicator when a first condition is met.

13 Claims, 3 Drawing Sheets

(51) Int. Cl.
  *G16H 30/40* (2018.01)
  *G16H 40/63* (2018.01)
  *A61B 3/113* (2006.01)

(52) U.S. Cl.
  CPC .......... *A61B 5/7445* (2013.01); *G16H 30/40* (2018.01); *G16H 40/63* (2018.01); *A61B 3/113* (2013.01)

(58) Field of Classification Search
  USPC ............... 600/300–301, 595; 715/708–709; 361/679.01–679.03; 345/633
  See application file for complete search history.

(56) References Cited

U.S. PATENT DOCUMENTS

| | | | |
|---|---|---|---|
| 6,800,062 | B2 | 10/2004 | Epley |
| 2004/0097839 | A1 | 5/2004 | Epley |
| 2005/0099601 | A1 | 5/2005 | Macdougall et al. |
| 2007/0161875 | A1* | 7/2007 | Epley .................. A61B 5/0484 600/301 |
| 2007/0261702 | A1* | 11/2007 | Bromwich ........... A61B 5/1126 128/897 |
| 2008/0058681 | A1 | 3/2008 | Casali et al. |
| 2010/0228144 | A1 | 9/2010 | Labat |
| 2010/0331721 | A1 | 12/2010 | Epley |
| 2011/0275959 | A1* | 11/2011 | Casali .................. A61B 3/0083 600/595 |
| 2011/0282130 | A1 | 11/2011 | Krueger |
| 2014/0358009 | A1 | 12/2014 | O'Leary et al. |
| 2014/0375680 | A1* | 12/2014 | Ackerman ............ G06T 19/006 345/633 |
| 2015/0005587 | A1 | 1/2015 | Qu et al. |
| 2015/0335239 | A1 | 11/2015 | Macfougall |

FOREIGN PATENT DOCUMENTS

| | | |
|---|---|---|
| JP | 2005-304912 A1 | 11/2005 |
| WO | WO 2012/065600 A2 | 5/2012 |

OTHER PUBLICATIONS

Extended European Search Report dated Sep. 16, 2015, for corresponding European Patent Application No. 15161784.2, 9 pages.
First Technical Examination dated Jun. 30, 2015, for corresponding Danish Patent Application No. PA 2015 70187, 8 pages.

* cited by examiner

VESTIBULAR TESTING APPARATUS

RELATED APPLICATION DATA

This application claims priority to and the benefit of Danish patent application No. PA 2015 70187, filed Mar. 30, 2015, pending, and European patent application No. 15161784.2, filed Mar. 30, 2015, pending. The entire disclosures of both of the above applications are expressly incorporated by reference herein.

FIELD

This disclosure relates to an apparatus for diagnosing and treating vertigo, dizziness and similar balance-related disorders in a human being.

BACKGROUND

Dizziness is a common condition affecting a large part of the population. The diagnostic and treatment for vestibular disorders requires that a patient be placed with their head in particular positions, e.g. the patient is sitting upright with the head straight and not moving. In order to perform diagnosis or treatment the patient may need to be moved to a particular position or to a predetermined set of positions in a specific order. The proper positioning of the patient's head is essential for proper diagnosis and treatment.

Since vestibular activity (i.e. a person's reaction to changes in orientation, "sense of balance") cannot be monitored directly in a patient, a physician has to rely on secondary indications, such as the eye movement reflex, for objectively detecting activity in a person's vestibular system. When the head rotates about any axis, a person will inherently and involuntarily try to sustain distant visual images by rotating his or her eyes in the opposite direction on the respective axis. The semi-circular canals in the inner ear sense angular momentum and send signals to the nuclei for eye movement in the brain. From here, a signal is relayed to the extraocular muscles to allow his or her gaze to fixate on one object as the head moves. A particular reaction denoted nystagmus occurs when the semi-circular canals are being stimulated while the head is not in motion. The direction of eye movement is directly related to the particular semi-circular canal being stimulated.

One example of a condition which may be diagnosed and treated is Benign Paroxysmal Positional Vertigo (BPPV). BPPV is the most common cause of vertigo, accounting for nearly 40% of all vertiginous patients. The most common cause for BPPV is a displacement of the calcium-carbonated crystals (otolithic stones) present in the utricle into the semi-circular canal (canalithiasis) or onto the cupula (cupulathiasis) of the patient. Today, posterior canal BPPV (the most common) is diagnosed by performing a special sequence of particular positionings of the patient denoted a Dix-Hallpike maneuver, while the examiner simultaneously looks for nystagmus by observing the eyes when the patient is in a supine position with his or her head turned towards the affected ear. The Dix-Hallpike maneuver is the most common positioning sequence in use for diagnosing BPPV but other maneuvers such as Hallpike-Stenger, side-lying and roll are also used. The maneuver chosen is determined by physician preference, patient's neck mobility and a suspicion of whether the BPPV is present in the posterior, anterior or lateral semi-circular canal, respectively. The treatment for BPPV is through a repositioning maneuver. There are several repositioning maneuvers available to the physician for this purpose, e.g. Canalith Repositioning Treatment (denoted the Epley maneuver), Liberatory (denoted the Semant maneuver) and the so-called BBQ roll maneuver.

The maneuvers are successful in 90% of all patients treated in this manner. However, nearly 40% of the treated patients do experience reoccurrences and may need to return to the physician for additional repositioning. Why almost 40% of the treated patients do not experience immediate or lasting success from the treatment is not known. One reason could be that the repositioning maneuver may not have been properly performed by the physician. If the physician had the means to perform the repositioning maneuver at his disposal while at the same time keeping track of the patient's position and response, then the repositioning maneuver could be performed with a higher degree of confidence by the physician and a lot more patients would thus experience success from the treatment.

SUMMARY

A method may be performed for observing and identifying abnormal human vestibular activity. The method may involve invoking a selected spatial orientation in a person and providing a visual representation of the spatial orientation of the person and one or more motion components of the vestibular activity of the person. The method may permit the automatic performance of e.g. the Dix-Hallpike maneuver while monitoring the vestibulo-spinal reflex as an indication of the change in spatial orientation together with monitoring the spatial orientation. An apparatus may be configured to perform the above method, and may include positioning or orientation measurement for determining the position of a patient's head, e.g. accelerometers or similar devices, and eye movement monitoring equipment, e.g. goggles or glasses mounted on the head of the patient and provided with cameras or similar equipment in order to register eye movements of the patient. In some cases, the apparatus may further comprise a mechanism for suspending the patient in a freely rotatable, arbitrary 360° spatial orientation during the performance of the test, the mechanism being capable of altering the spatial orientation of the patient automatically according to the requirements for triggering the desired response during the test.

The apparatus described above may demand a fair degree of training and experience by the physician or assistant performing the test in situations where there is no mechanism for automatically altering the spatial orientation of the patient. Even if such mechanism is available, it may be bulky and expensive, and may thus only be accessible to physicians having the necessary space and funding to obtain and use such a mechanism.

Thus, it may be desirable to have a cost-effective method and a system for observing and identifying abnormal human vestibular activity during testing or treatment which is easy to use by a physician with a minimum of additional training without taking up a lot of space.

According to some embodiments, a system for detecting and recording head orientations of a person is devised, said system comprising a first sensor device capable of acquiring at least sensor data regarding a person's head orientation in three-dimensional space, a computing system comprising, a medical data acquisition system, a processor, and a graphical display, wherein the medical data acquisition system is configured for storing and outputting sensor data from the first sensor device, the graphical display is configured for displaying images generated by the processor, and the processor is configured for processing the sensor data from the medical data acquisition system, outputting a first signal representing head orientation and generating images suitable for being shown by the graphical display, said images comprising at least; a first reference indicator, an orientation indicator, wherein the position of said orientation indicator, e.g. with relation to the first reference indicator, in the graphical display is determined based on the first signal from the processor, and a feedback signal whenever a first specific condition is met. This allows a physician to follow manipulations of the orientation of the person in a precise and secure way without involving the use of bulky equipment or elaborate training.

In one embodiment, the first specific condition is that the first signal representing a head orientation deviates more than a predetermined amount from a head orientation according to a particular maneuvering scheme. In another embodiment, the first specific condition is that the orientation indicator deviates more than a predetermined amount from a desired position with relation to the first reference indicator according to a particular maneuvering scheme. This allows the display of the system to provide fast and effective feedback to the physician during the performance of head movements of the person being examined or treated.

In an embodiment, the processor generates the feedback signal by changing the color, the shape or the size of the orientation indicator in the graphical display. In an embodiment, the system comprises a memory configured for holding at least a stored, three-dimensional model of a human head. In a further embodiment, the images generated by the processor comprises a two-dimensional projection of the stored, three-dimensional model of a human head, wherein the viewing angle of the two-dimensional projection is determined based on the first signal representing head orientation. In another embodiment, the first reference indicator is configured for providing feedback regarding rotations about a first local axis, and a second reference indicator is configured for providing feedback regarding rotations about a second local axis perpendicular to the first local axis. The feedback signal together with the changes in the viewing angle of the two-dimensional projection of the three-dimensional model of a human head makes it easy for the physician to follow the orientation of the person's head continuously during examination and immediately correct any deviations from the predetermined head rotation.

In an embodiment, the system comprises a second sensor device capable of acquiring sensor data regarding a person's eye movements, and the processor is configured for deriving vestibular activity from the sensor data regarding a person's eye movements provided by the second sensor device. In further embodiments, the stored, three-dimensional model of a human head of the memory comprises stored, three-dimensional models of a left set of semi-circular canals and a right set of semi-circular canals, respectively. The processor, in an embodiment, is configured to provide a two-dimensional projection of the stored, three-dimensional models of the sets of semi-circular canals and to change the color of the individual semi-circular canals of the left set of semi-circular canals and the right set of semi-circular canals, respectively, in response to the derived vestibular activity. The two-dimensional projections of the models of the semi-circular canals of the left set of semi-circular canals and the right set of semi-circular canals, respectively, changes their viewing angle with the viewing angle of the two-dimensional projection of the three-dimensional model of a human head and, in addition, changes their appearance individually whenever vestibular activity is detected by the acquired data regarding the person's eye movements, e.g. by changing color. This feature allows the physician to follow vestibular activity of the person being examined or treated during head manipulations, thus making it easier for the physician to determine abnormal vestibular responses from the person during examination or treatment.

In some embodiments, the particular maneuvering scheme is selected from the group consisting of a Dix-Hallpike maneuver, an Epley maneuver or a Semant maneuver. An embodiment provides the particular maneuvering scheme is selected prior to detecting vestibular activity in a person. This feature allows the physician to select, e.g. a Dix-Hallpike maneuver prior to performing it on the person being examined and to have the system aid the individual movements of the maneuver precisely and in the correct sequence, since the system is capable of 'knowing' in advance that a Dix-Hallpike maneuver is to be performed, provide a sequence of expected head-turning angles for guidance and thus possesses the capability to guide the physician during performance of the maneuver.

A system for detecting and recording head orientations of a person includes: a first sensor device capable of providing sensor data regarding a head orientation of a person in a three-dimensional space; a medical data acquisition system configured for storing and outputting the sensor data from the first sensor device; and a processor configured for processing the sensor data from the medical data acquisition system, outputting a first signal representing the head orientation, and generating an image for presentation by a graphical display; wherein the image comprises: a first reference indicator; an orientation indicator, wherein a position of the orientation indicator in the image is determined based on the first signal from the processor, and a feedback indicator when a first condition is met.

Optionally, the first condition is met when the head orientation represented by the first signal deviates more than a predetermined amount from a desired orientation according to a maneuvering scheme.

Optionally, the maneuvering scheme comprises a Dix-Hallpike maneuver, an Epley maneuver, or a Semant maneuver.

Optionally, the maneuvering scheme is pre-determined prior to detecting vestibular activity in the person.

Optionally, the first condition is that the position in the image of the orientation indicator deviates more than a predetermined amount from a desired position in the image with relation to the first reference indicator according to a maneuvering scheme.

The first reference indicator may be formed like a ruler or a number line with numbers along the ruler or number line showing a signed distance from the number in question to a reference point marked with the number zero on the ruler or number line. The number may show in degrees, the angular rotation of the head around a first axis, for example a horizontal axis in which case the first reference indicator is preferably shown as a horizontal ruler or number line in the image. The orientation indicator may be positioned with relation to the first reference indicator at a position that corresponds to the current angular rotation of the head around the first, e.g. horizontal, axis. The first condition may be met, when the orientation indicator is outside a desired range of angular rotation around the first axis.

Optionally, the image comprises a second reference indicator.

The second reference indicator may be formed like a ruler or a number line with numbers along the ruler or number line showing a signed distance from the number in question to a reference point marked with the number zero on the ruler or number line. The number may show in degrees, the angular rotation of the head around a second axis. The second axis may be perpendicular to the first axis. The second axis may be a vertical axis in which case the second reference indicator is preferably shown as a vertical ruler or number line in the image. The orientation indicator may be positioned with relation to the second reference indicator at a position that corresponds to the current angular rotation of the head around the second, e.g. vertical axis. The first condition may be met, when the orientation indicator is outside a desired range of angular rotation around the second axis, or the first condition may be met, when the orientation indicator is outside a desired range of angular rotation around the first axis and/or is outside a desired range of angular rotation around the second axis.

Optionally, the orientation indicator may have the form of an image of a Cartesian coordinate system, e.g., with the x-axis, y-axis, and z-axis defined below with relation to a person's head, and the orientation of which may be shown in the image with relation to another Cartesian coordinate system forming the first reference indication and, e.g., having a horizontal x-axis and a horizontal y-axis and a vertical z-axis, e.g. corresponding to a desired starting position of the person's head of a selected maneuvering scheme. Thus, optionally, at the desired starting position of the person's head, the orientation indicator and the first reference indicator coincide, and the as the person's head is rotated desirably in accordance with the selected maneuvering scheme, the orientation indictor is shown in the image in positions corresponding to the current rotation of the person's head, and the first condition may be met when the orientation indicator is outside a desired range of angular rotation, e.g., around the x-axis, y-axis and z-axis.

Optionally, the feedback indicator comprises a change in a color, a shape, or a size of the orientation indicator.

Optionally, the system further includes a memory configured for storing a three-dimensional model of a human head.

Optionally, the feedback indicator comprises a change in a color, a shape, or a size of (1) a two-dimensional projection of the three-dimensional model of the human head, (2) the first reference indicator or (3) a second reference indicator.

Optionally, the three-dimensional model of the human head comprises a first three-dimensional model of a left set of semi-circular canals and a second three-dimensional model of a right set of semi-circular canals.

Optionally, the image generated by the processor comprises a two-dimensional projection of the three-dimensional model of the human head, wherein a viewing angle of the two-dimensional projection is determined based on the first signal representing the head orientation.

Optionally, the image generated by the processor comprises a second reference indicator.

Optionally, the first reference indicator is configured for providing a first feedback regarding a first rotation about a first local axis, and the second reference indicator is configured for providing a second feedback regarding a second rotation about a second local axis perpendicular to the first local axis.

Optionally, the system further includes a second sensor device capable of providing an additional sensor data regarding an eye movement of the person, wherein the processor is configured for deriving vestibular activity from the additional sensor data regarding the eye movement provided by the second sensor device.

Optionally, the system further includes a memory configured for storing a three-dimensional model of a human head; wherein the three-dimensional model of the human head comprises a first three-dimensional model of a left set of semi-circular canals, and a second three-dimensional model of a right set of semi-circular canals; and wherein the processor is configured to (1) provide a two-dimensional projection of the first three-dimensional model, the second three-dimensional mode, or both, and (2) to change a color of at least a part of the two-dimensional projection in response to the derived vestibular activity.

Optionally, the system further includes the graphical display.

One or more embodiments described herein provide a cost-effective method and a system for observing and identifying abnormal human vestibular activity during testing or treatment, which is easy to use by a physician with a minimum of additional training without taking up a lot of space. Accordingly, one or more embodiments described herein are advantageous over known apparatus and method, like those described in U.S. Pat. No. 6,800,062.

Other features and embodiments will be described below in the detailed description.

DESCRIPTION OF THE FIGURES

The embodiments are described in greater detail in the following, where.

DETAILED DESCRIPTION

Figure 1:
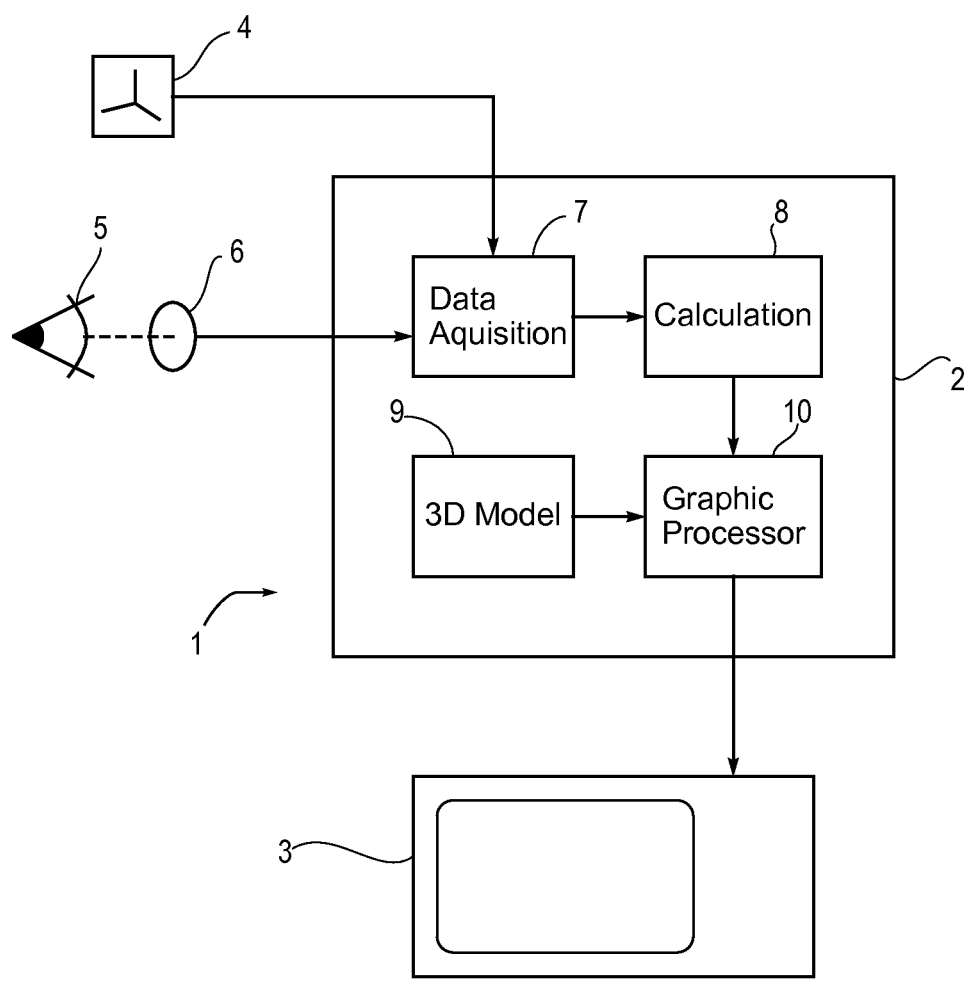
FIG. 1 is a block schematic illustrating a vestibular testing apparatus.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The block schematic in FIG. 1 illustrates a clinical setup 1 for testing and examining vestibular activity in a person. The clinical setup 1 comprises a computerized system 2, an eye movement detector 6 for detecting movements of an eye 5 of the person being examined, an orientation sensor 4 for detecting the orientation of the person, and a display 3 for displaying orientation and vestibular activity in real time during an examination. The computerized system 2 comprises a data acquisition module 7, a calculation module 8, a memory 9 holding a three-dimensional model of a head and semi-circular canals of a person, and a graphic processor 10 for providing an output signal for the display 3. The computerized system 2 may be embodied as a dedicated computing device or it may be embodied as an application designed for execution on a standard off-the-shelf personal computer.

The eye movement detector 6 and the orientation sensor 4 may be built into a self-contained, head-mountable unit (not shown in FIG. 1), e.g. of the kind described in European patent application EP 14169653.4. The head-mountable unit is a relatively small and lightweight piece of hardware allowing a person to move his or her head freely while wearing the unit. The head-mountable unit may preferably be embodied as a pair of goggles fixable to a person's head by e.g. an adjustable headband. The eye movement detector 6 may be embodied as a small video camera constantly monitoring the eye of the person, e.g. via a semi-transparent mirror. The eye movement detector 6 may be doubled for the purpose of monitoring movement of both the left eye and the right eye of a person simultaneously. The orientation sensor 4 may be embodied as an accelerometer unit mounted on the head-mountable unit. During examination, the head-mountable unit is fixed to the head of the person being examined, and data regarding eye movements and spatial orientation are fed to the data acquisition module 7 of the computerized system 2. Prior to performing a proper examination of the person, an orientation calibration procedure is performed in order to be able to coordinate the data collected from the head-mountable unit correctly with a reference equilibrium position of the person.

During an examination of the person wearing the calibrated, head-mountable unit, the person's head is placed in a series of different positions or orientations by the physician performing the examination while the physician watches the display 3 of the clinical setup 1. By looking at the display 3 during the examination the physician may monitor the actual orientation and the vestibular reactions of the person being examined. The vestibular reactions are reflected in involuntary movements of the eyeballs of the person and the data from the eye movement detector 6 are thus used by the calculating module 8 for calculating the corresponding vestibular reactions. The results of the calculations are provided to the graphic processor 10 and combined with a stored, three-dimensional model of a human head and a pair of associated semi-circular canals provided by the dedicated memory 9 for the purpose of generating a real time, two-dimensional perspective projection of a human head and semi-circular canals in a viewport of the display 3 for viewing by the physician performing the examination.

Figure 2:
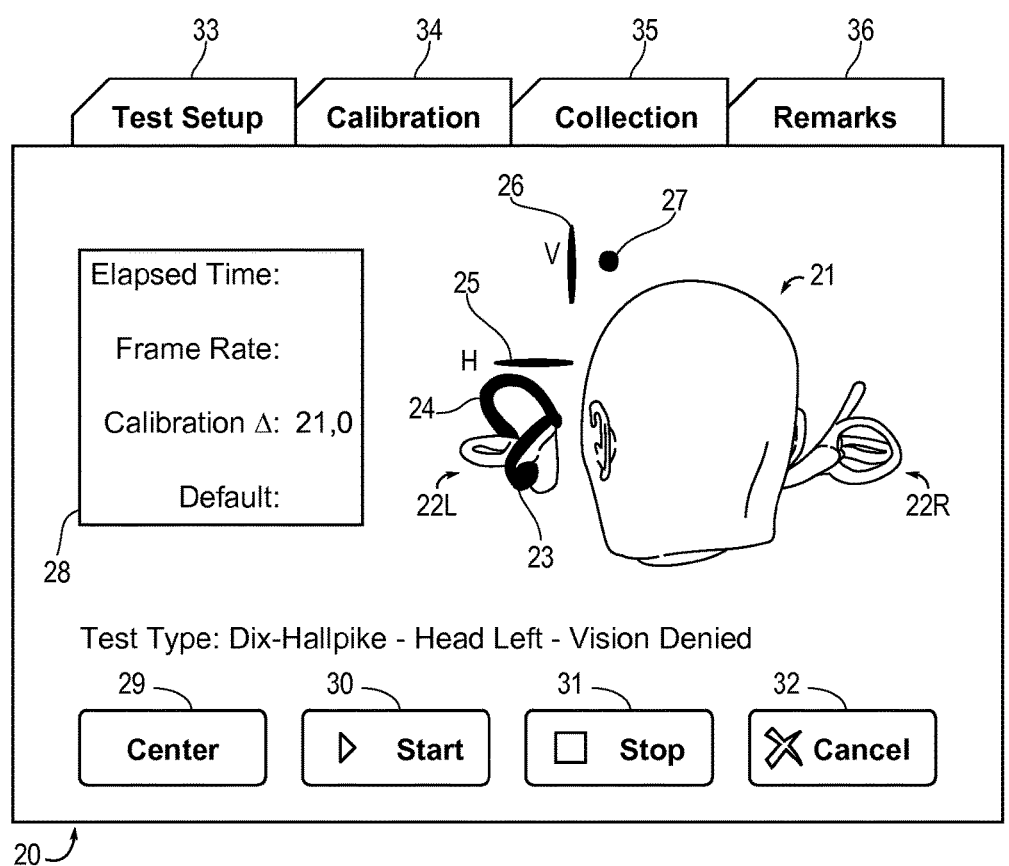
FIG. 2 illustrates an exemplary display showing a vestibular response and head direction.

An exemplary picture, as it may be provided by the display 3 of FIG. 1, is illustrated in FIG. 2. FIG. 2 shows a main window 20 comprising a perspective projection of a human head 21, a data window 28, a set of operating controls 29, 30, 31, 32 and a set of tabbed windows 33, 34, 35 and 36. The perspective projection of the human head 21 further comprises a set of left semi-circular canals 22L, a set of right semi-circular canals 22R, a horizontal reference indicator 25, e.g. constituting an example of the first reference indicator, a vertical reference indicator 26, e.g. constituting an example of the second reference indicator, and an orientation indicator 27. The orientation indicator 27 represents a two-dimensional projection of the head orientation of the person as determined by the orientation sensor 4. In the perspective projection 21, the left set of semi-circular canals 22L has a posterior semi-circular canal 23 and an anterior semi-circular canal 24 emphasized by a dark color indicating vestibular activity in those canals. For clarity, the left and right sets of semi-circular canals 22L and 22R, respectively, are shown as floating in space some distance from the human head 21 in the main window 20.

During use of the system 1, the physician initiates a data collection session by calibrating the head-mountable unit by activating the "Center" button 29 in the main window 20. This calibration is done with the person's head carrying the head-mountable unit and facing straight forward. Any subsequent movements the person's head makes after calibration is then recorded and shown relative to the calibration point. When the person moves his or her head in space, the perspective projection angle of the human head 21 moves correspondingly in the main window 20, the perspective projection angle of the set of left semi-circular canals 22L and the set of right semi-circular canals 22R moving along with the human head 21 while keeping their relative positions with respect to the human head 21. When the calibration procedure has finished, the physician may start the acquisition of movement and vestibular response data by activating the "Start" button 30 in the main window 20.

Moving together with the perspective projection of the human head 21 is the orientation indicator 27. When the person's head moves, the orientation indicator 27 will move correspondingly with respect to the vertical reference indicator 26 and the horizontal reference indicator 25, respectively. The positioning of the vertical reference indicator 26 and the horizontal reference indicator 25 is determined by the type of examination to be performed. In the case of e.g. the physician wishing to perform a Dix-Hallpike maneuver with the aid of the system 1, the physician has to move the person's head about an axis going vertically through the head of the person in a first move and about an axis going from ear to ear of the person in a second move. The orientation indicator 27 aids the physician in performing the Dix-Hallpike maneuver by making the physician move the person's head in such a way that the orientation indicator 27 stays on the vertical reference indicator 26 during the first movement and the orientation indicator 27 stays on the horizontal reference indicator 25 during the second movement. Preferably, orientation indicator 27 may light up or change color if the orientation indicator 27 is veering off track during the first or the second movement. An angle tolerance may be built into the system.

In this way, the display 3 of the system 1 may provide positive feedback to the physician in real time during performance of e.g. the Dix-Hallpike maneuver, guiding the movements the physician has to perform on the patient's head and/or torso in order to retrieve the desired examination or treatment results. The combination of the two-dimensional projection of the head 21, the two sets of semi-circular canals 22L and 22R and the orientation indicator 27 with respect to the vertical reference indicator 26 and the horizontal reference indicator 25 provides for a high degree of precision in the movements of the person's head. Due to the fact that the eye movement detector 6 is monitoring the eyes of the person, the system may indicate e.g. the presence of nystagmus by making individual semi-circular canals of the two-dimensional projection of the semi-circular canals 22L and 22R light up or change color in the window 20, thus indicating vestibular activity in those semi-circular canals. This is indicated in FIG. 2 as the left posterior semi-circular canal 23 and the left anterior semi-circular canal 24 being dark in color indicating activity in the left posterior semi-circular canal and the left anterior semi-circular canal of the person being examined.

Some types of examination may require the person being tested to be vision denied, i.e. blindfolded. This is due to the fact that it is natural to most people to use their eyesight in order to determine their orientation in space. In order to exclude this sensory modality from the examination, the person being examined may wear dark or opaque eye coverings on one or both eyes during examination or treatment. The eye coverings are preferably placed beneath the goggles when worn by the person and are manufactured from a material blocking all light but the infrared range of the electromagnetic spectrum, thus rendering the person without any visual cues for the duration of the examination. The eye movement detector 6 of the system 1 is configured to be sensitive in the infrared range of the spectrum, thereby permitting detection of eye movements even though the person being examined cannot see anything. Since the balance reflex of the eyes is present even if the person does not see anything, this strategy of examination effectively excludes visual cues from the examination, thus effectively isolating the signals from the balance organs for detailed analysis during or after the examination.

During an examination, the data acquisition module 7 of the computerized system 2 in FIG. 1 provides the calculation module 8 with streams of real time data representing gaze direction and spatial orientation of the head of the person being examined. These data are sorted, filtered and recorded by the calculation module 8 and converted into a vector representing spatial orientation and vestibular activity in both sets of semi-circular canals 22L and 22R, respectively. This vector is provided to a first input of the graphic processor 10 for the generation of the real time two-dimensional projection of a human head 21 shown in FIG. 2. Simultaneously, the stored three-dimensional model of a human head and associated semi-circular canals provided by the dedicated memory 9 is applied to a second input of the graphic processor 10 for calculating the projection of a proper two-dimensional representation of a human head 21 and corresponding left and right sets of semi-circular canals 22L and 22R, respectively, suitable for being shown on the display 3.

A three-dimensional coordinate system is defined as a standard right-hand coordinate system, where the x-axis goes from ear to ear in a person's head, the y-axis goes from the top of the person's parietal bone through the neck, and the z-axis goes from the back of the person's head to the tip of the nose. This coordinate system will be referred to in the following. Orientation angles of a human head about the three axes x, y and z may be expressed as Tait-Bryan chained rotations using three rotational matrices, where $$\vec{M}_x(\alpha) = \begin{bmatrix} 1 & 0 & 0 \\ 0 & \cos\alpha & -\sin\alpha \\ 0 & \sin\alpha & \cos\alpha \end{bmatrix},$$

$$\vec{M}_y(\beta) = \begin{bmatrix} \cos\beta & 0 & -\sin\beta \\ 0 & 1 & 0 \\ \sin\beta & 0 & \cos\beta \end{bmatrix}$$

and $$\vec{M}_z(\gamma) = \begin{bmatrix} \cos\gamma & -\sin\gamma & 0 \\ \sin\gamma & \cos\gamma & 0 \\ 0 & 0 & 1 \end{bmatrix}.$$

The three rotational angles $\alpha$, $\beta$, and $\gamma$ expressed in radians, describe the rotation of a human head about the three axes with respect to the origin (set at calibration time). Data provided by the rotation sensor 4 in FIG. 1 is used to calculate the rotation angles of the head of the person being examined. At calibration time, the rotational angles $\alpha$, $\beta$, and $\gamma$ are zero, and the data from the rotation sensor 4 is expressed as a vector, thus:

$$\vec{M}_{cal} = \begin{bmatrix} \alpha \\ \beta \\ \gamma \end{bmatrix} = \begin{bmatrix} 0 \\ 0 \\ 0 \end{bmatrix}$$

at calibration time, and $$\vec{M}_{x,y,z} = \begin{bmatrix} \alpha \\ \beta \\ \gamma \end{bmatrix}$$

during examination. The vector $\vec{M}_{x,y,z}$ is generated from data from the rotation sensor 4 by the data acquisition module 7, and is used as input for the calculation module 8.

Anatomically, the three semi-circular canals of a human being are denoted the lateral semi-circular canal (operating around a vertical axis in the transversal plane), the anterior semi-circular canal (operating around an anterial-posterial axis in the coronal plane) and the posterior semi-circular canal (operating around a lateral axis in the sagittal plane). As stated in the foregoing, the activity of the semi-circular canals cannot be monitored directly. Instead, the vestibulo-ocular reflex is used for detecting vestibular activity during examination using the eye movement detector 6. If, for instance, the head of the person being examined moves from left to right in the transversal plane, the person's eyes will move in the opposite direction from right to left thanks to the vestibulo-ocular reflex. The eye movement detector 6 records this behaviour and interprets it as a horizontal movement vector $\vec{E}_h$. If the person's head instead is moved up and down in the sagittal plane, the person's eyes will move down and up, respectively. The eye movement detector 6 records and interprets this behaviour as a vertical movement vector Finally, if the person's head is tilted and rotated in the coronal plane, the person's eyes will rotate in the opposite direction. The eye movement detector 6 records these eye movements and interprets the behaviour as a rotational movement vector $\vec{E}_r$. The way that the movement vectors $\vec{E}_h$, $\vec{E}_v$ and $\vec{E}_r$ are derived from the eye movement detector 6 is beyond the scope of this application.

The vectors $\vec{E}_h$, $\vec{E}_v$ and $\vec{E}_r$ are also used as inputs for the calculation module 8 for the purpose of deriving a set of vectors indicating the presence of a vestibular stimulus to a particular semi-circular canal. This set of vectors may be derived in the following manner:

The vectors are normalized;

$$\frac{\vec{E}_h}{\|\vec{E}_h\|} = \hat{E}_h,$$

$$\frac{\vec{E}_v}{\|\vec{E}_v\|} = \hat{E}_v,$$

and $$\frac{\vec{E}_r}{\|\vec{E}_r\|} = \hat{E}_r.$$

For the left eye, a stimulus vector $\vec{L}$ is derived:

$$L_{lateral} = k_1 \hat{E}_h,$$
$$L_{anterior} = k_2 \hat{E}_v$$
and
$$L_{posterior} = k_3 \hat{E}_r,$$

$$\vec{L} = \begin{bmatrix} L_{lateral} \\ L_{anterior} \\ L_{posterior} \end{bmatrix},$$

where $k_1$, $k_2$ and $k_3$ are constants.

Similarly, for the right eye, a stimulus vector $\vec{R}$ is derived:

$$R_{lateral} = k_1 \hat{E}_h,$$
$$R_{anterior} = k_2 \hat{E}_v$$
and
$$R_{posterior} = k_3 \hat{E}_r,$$

$$\vec{R} = \begin{bmatrix} R_{lateral} \\ R_{anterior} \\ R_{posterior} \end{bmatrix}.$$

The constants $k_1$, $k_2$ and $k_3$ are chosen in such a way that the individual values of $L_{lateral}$, $L_{anterior}$, $L_{posterior}$, $R_{lateral}$, $R_{anterior}$ and $R_{posterior}$ may take on the value of 0 or 1, respectively. The vectors $\vec{M}$, $\vec{L}$ and $\vec{R}$ are used by the calculation module 8 as inputs for the graphic processor 10.

During use, the graphic processor 10 takes the three-dimensional representation of a human head provided by the dedicated memory 9 and generates a two-dimensional representation of it by applying the vector $\vec{M}$ to the three-dimensional representation, generating a two-dimensional projection angle for the representation. Next, the graphic processor 10 takes the stimulus vectors $\vec{L}$ and $\vec{R}$, respectively, and uses them to determine the color of the individual semi-circular canals of the set of semi-circular canals 22L and 22R of the projection of the human head shown in the main window 20 of FIG. 2. When there is no significant activity in the semi-circular canals of the person being examined, as derived from the vectors $\vec{E}_h$, $\vec{E}_v$ and $\vec{E}_r$ provided by the eye movement detector 6, the semi-circular canals are depicted in a neutral color. Upon detection of vestibular activity in one or more of the semi-circular canals of the person being examined, in the manner described above, the graphic processor 10 changes the color of the semi-circular canals where activity is detected into a color deviating from the neutral color used to illustrate no vestibular activity, as illustrated by the semi-circular canals 23 and 24 in FIG. 2. In this way, the head orientation and the vestibular activity may be monitored simultaneously on the display 3 of the system 1 during examination of a person wearing the rotation sensor 4 and the eye movement detector 6.

In order to provide a more secure and precise indication of the person's head during the performance of e.g. a Dix-Hallpike maneuver, additional indicators are provided in the main window 20 of the display 3 in the form of the horizontal reference indicator 25, the vertical reference indicator 26 and the orientation indicator 27. The orientation indicator 27 is a two-dimensional projection of a three-dimensional point P onto an imaginary plane F in front of the two-dimensional representation of a human head 21. The plane F is perpendicular to the vector $\vec{M}_{cal}$. The point P is defined as the point where the vector $\vec{M}_{x,y,z}$ intersects with the imaginary plane F. This may be expressed as:

$$F = t\vec{M}_{x,y,z} = P, \text{ where } t \in \mathbb{R}.$$

In other words, the orientation indicator 27 follows the direction of the head of the person being examined closely whenever the head is turned about one of its three axes. During setup of a Dix-Hallpike maneuver, the horizontal reference indicator 25 and the vertical reference indicator 26 are projected onto the plane F in such a way that the orientation indicator 27 coincides with the vertical reference indicator 26 during a first correct movement of the Dix-Hallpike maneuver, and the orientation indicator 27 coincides with the horizontal reference indicator 25 during a second correct movement of the Dix-Hallpike maneuver. The horizontal reference indicator 25 and the vertical reference indicator 26 both have an elongated shape when displayed in the main window 20, and this feature makes it easy for the physician to follow with the movements of the head of the person being examined. By providing the system 1 with a tolerance of e.g. five degrees in either direction, the physician may be easily alerted whenever a movement diverts too much from the correct movement, e.g. by having the orientation indicator 27 change color, texture or general appearance in such cases, allowing the physician to perform corrections of the movements in a secure and easy manner. The way an examination is performed using the system 1 is described in greater detail in the following.

If the Dix-Hallpike maneuver is chosen for detecting e.g. BPPV in the left set of semi-circular canals in a person being examined, this choice may be input to the system 1 in the test setup tab 33 in the main window 20 in FIG. 2. The system 1 now shows the horizontal reference indicator 25 and the vertical reference indicator 26 in the main window 20. The person being examined is sitting upright on an examination couch and in a first step of the Dix-Hallpike maneuver has his or her head turned 45° to the side being tested (i.e. the left side in this case). With the head still turned in this fashion, the person is laid down on the back on the examination couch rather quickly in such a way that the head is tilted further 20°-30° backwards. During this part of the Dix-Hallpike maneuver, the physician performing the maneuver watches the main window 20 on the display 3, especially keeping an eye on the orientation indicator 27. The orientation indicator 27 moves about in the main window 20 when the head of the person being examined moves, and usually represents the gaze direction of the person. If the head angle differs too much from the expected 45°, or if the movement of the person being examined into the lying position is too slow, the orientation indicator 27 in the main window 20 changes color, e.g. to a red color, in order to guide the physician to a proper execution of the movement. During a second step of the Dix-Hallpike maneuver, the person being examined is returned to an upright sitting position while keeping the head turned 45° to the left, the physician still keeping an eye on the orientation indicator 27 in order to provide the right velocity and angles for the second step of the Dix-Hallpike maneuver.

During the performance of the Dix-Hallpike maneuver, the system 1 records and displays the movements and reactions of the person being examined. The head angle is reflected in the two-dimensional representation of a human head 21 in the main window 20 allowing the physician to follow the head orientations in a precise manner during examination. The reactions of the vestibular systems of the person being examined are being reflected in the two-dimensional representation of the semi-circular canals 22L and 22R displayed along with the human head representation 21, allowing the physician to monitor the vestibular reactions of the person being examined in real time during examination. The horizontal reference indicator 25 and the vertical reference indicator 26 provides a guidance for the physician performing the movements of the Dix-Hallpike maneuver, using the positioning and coloring of the orientation indicator 27 as an aid in the movements.

When the Dix-Hallpike maneuver has been performed, the physician may browse through the recorded data by selecting the "Collection" tab 35 of the main window 20 and perform subsequent analyses aided by the recorded data set in order to establish accurate diagnoses, e.g. of BPPV. The mechanism of the aid provided by the system 1 is described more closely with reference to FIGS. 3a and 3b.

Figure 3A:
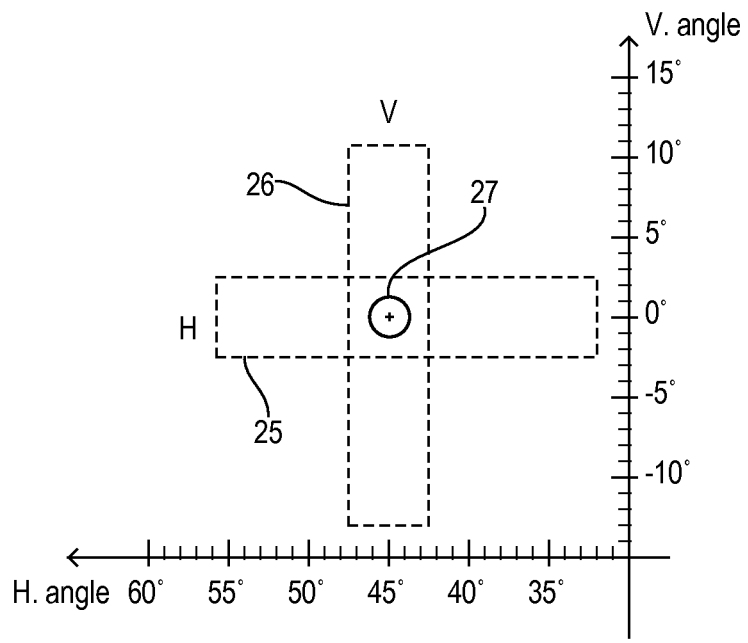
FIG. 3a illustrates a direction target in a correct position during a head movement.

In FIG. 3a is illustrated an orientation indicator 27 right after performance of a first step in a Dix-Hallpike maneuver. As stated in the foregoing, the first step of a Dix-Hallpike maneuver involves turning the head of the person being examined 45° from the origin about the vertical axis towards the suspected affected side, in this case the left side, while keeping the head straight up. The orientation indicator 27 will move about in the display 3 as the head is turned, in this case to the left side. In FIG. 3a, the orientation indicator 27 is at the 45° mark on the horizontal axis and at 0° on the vertical axis. Also shown in FIG. 3a is a vertical box V and a horizontal box H. As indicated in FIG. 3a, these boxes represents the horizontal reference indicator 25 and the vertical reference indicator 26 in FIG. 2 and illustrate the limits within which the orientation indicator 27 is deemed to be 'correctly' positioned horizontally and vertically. As long as the center of the orientation indicator 27 is within those limits, the orientation indicator 27 is assigned a pale, or neutral color by the system when shown in the main window 20 in FIG. 2. The rotational tolerance limits of a first step of a Dix-Hallpike maneuver is from about 42° to approximately 47° from the origin in the horizontal plane and from approximately −3° to around 3° from the origin in the vertical plane. These limits are selected for illustrative purposes only and are chosen arbitrarily in the examples shown in FIGS. 3a and 3b.

Figure 3B:
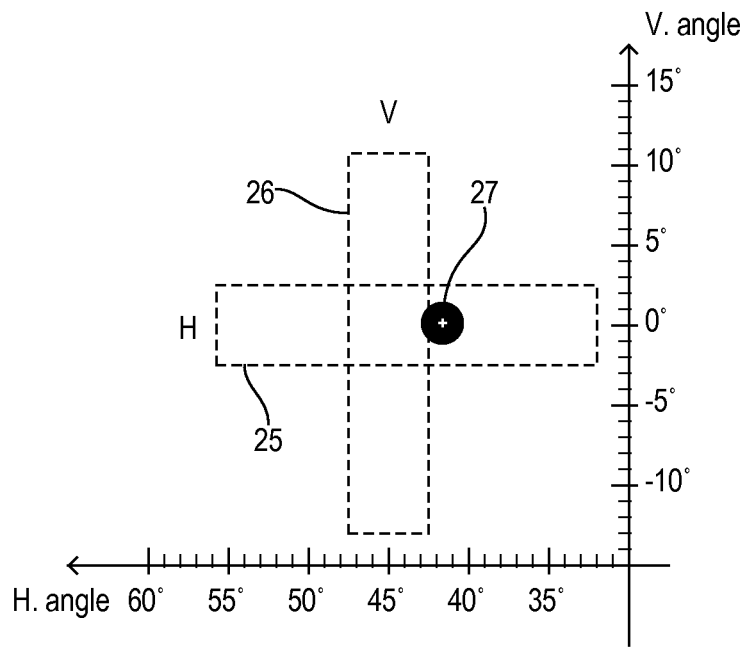
FIG. 3b illustrates a direction target in an incorrect position during a head movement.

In FIG. 3b is illustrated an orientation indicator 27 right after performance of a first step in a Dix-Hallpike maneuver. In this case, however, the physician has not turned the head of the person being examined sufficiently far to the left, but only to about 41° from the origin. The orientation indicator is still at 0° along the vertical axis in FIG. 3b. Since the orientation indicator 27 is now outside the predetermined limits defined by the vertical box V, the feedback condition is now met and the orientation indicator 27 is assigned a darker, contrasting color by the system when shown in the main window 20 in FIG. 2, thus providing a clear feedback signal to the physician that the head of the person being examined has not been turned sufficiently far to the left in the first step of the Dix-Hallpike maneuver. As soon as the physician turns the head of the person being examined sufficiently further to the right to have the orientation indicator 27 fall within the limits of the vertical box V, the feedback condition ceases to be met and the orientation indicator 27 will therefore change back to a neutral color in the main window 20 again. If the turn of the head is overshot, for instance by turning the head of the person being examined further than approximately 47°, the feedback condition is met once again and the orientation indicator 27 will again change to a contrasting color indicating a maneuver error by the physician.

A variety of vestibular conditions may be diagnosed or alleviated using the system 1. An example of a procedure which alleviates BPPV is the Epley repositioning maneuver, which works by allowing free-floating particles located within the affected semi-circular canal to flow back from the semi-circular canal to the utricle of the inner ear by the straightforward means of gravity. The Epley maneuver involves a sequence of manipulations with a patient similar to the Dix-Hallpike maneuver, but is a bit more involved and thus more difficult to perform correctly. Having used the system 1 and e.g. the Dix-Hallpike maneuver to determine the extent and location of the cause of BPPV in a person, the physician may set up the system 1 in a similar manner in order to perform the Epley maneuver while observing the main window 20 for guidance during the various steps of the Epley maneuver. The physician may subsequently perform the Dix-Hallpike maneuver again in order to determine if, and to what degree, the Epley maneuver have provided an improvement to the patient.

Thanks to the elaborate guidance means provided by the main window 20 of the display 3 of the system 1, the physician may perform a wide range of different, vestibular examinations quickly and securely, without worrying if the movements performed of the person being examined or treated are sufficiently accurate to be effective.

In a preferred embodiment, the eye movement detector 6 and the rotation sensor 4 of the system 1 are built into a pair of lightweight goggles, e.g. of the kind described in European patent application EP 14169653.4. The processing of data from the sensors of the goggles may be executed on a standard personal computer running suitable software providing the functionality of the computerized system 2 of the system 1. Data acquisition, recording and storage may be provided by the standard storage means provided by the personal computer, and means for subsequent analysis of the data recorded during the examinations may also be provided by the software.

The system according to one or more embodiments described herein provides an improvement of diagnosis and treatment of a variety of ailments in the vestibular system of a person and is especially useful in diagnosing and treating people suffering from BPPV.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. A system for detecting and recording head orientations of a person, comprising:
   a first sensor device capable of providing sensor data regarding a head orientation of a person in a three-dimensional space;
   a second sensor device capable of providing an additional sensor data regarding an eye movement of the person;

a medical data acquisition system configured for storing and outputting the sensor data from the first sensor device and the additional sensor data from the second sensor device;

a memory configured for storing a three-dimensional model of a human head and semi-circular canals of the person;

a calculation module that receives streams of real time sensor data representing gaze direction and spatial orientation of the head of the person from the medical data acquisition system, for a series of different head orientations performed by a physician and converts the real time data into a horizontal movement vector, a vertical movement vector and a rotational movement vector representing spatial orientation and vestibular activity in the person; and a processor configured for processing and combining the real time vector data from the calculation module with the three-dimensional model of the human head and the semi-circular canals stored in the memory, outputting a first signal representing the head orientation, and generating an image having a two-dimensional projection of the three-dimensional model of the human head for presentation by a graphical display;

wherein the processor is configured for deriving the presence of vestibular activity from the additional sensor data regarding the eye movement provided by the second sensor device;

wherein the image comprises:

a first reference indicator;

a second reference indicator;

a set of left semi-circular canals, a set of right semi-circular canals;

an orientation indicator, wherein a position of the orientation indicator in the image is determined based on the first signal from the processor; and a feedback indicator for providing a feedback when a first condition is met, wherein the feedback indicator comprises a change in a color, a shape, or a size of a two-dimensional projection of the three-dimensional model of the human head, the first reference indicator or the second reference indicator;

whereby a viewing angle of the two-dimensional projection of the three-dimensional model of the human head is determined based on the first signal representing the head orientation and wherein the combination of the two-dimensional projection of the head, the two sets of left and right semi-circular canals and the orientation indicator with respect to the first reference indicator and the second reference indicator provides a high degree of precision in the movements of the person's head.

2. The system according to claim 1, wherein the first condition is met when the head orientation represented by the first signal deviates more than a predetermined amount from a desired orientation according to a maneuvering scheme.

3. The system according to claim 2, wherein the maneuvering scheme comprises a Dix-Hallpike maneuver, an Epley maneuver, or a Semant maneuver.

4. The system according to claim 2, wherein the maneuvering scheme is pre-determined prior to detecting vestibular activity in the person.

5. The system according to claim 1, wherein the first condition is that the position of the orientation indicator in the image deviates more than a predetermined amount from a desired position with relation to the first reference indicator according to a maneuvering scheme.

6. The system according to claim 1, wherein the three-dimensional model of the human head comprises a first three-dimensional model of the set of left semi-circular canals and a second three-dimensional model of the set of right semi-circular canals.

7. The system according to claim 1, wherein the first reference indicator is configured for providing a first feedback regarding a first rotation about a first local axis, and the second reference indicator is configured for providing a second feedback regarding a second rotation about a second local axis perpendicular to the first local axis.

8. The system according to claim 1, further comprising a memory configured for storing a three-dimensional model of a human head;

wherein the three-dimensional model of the human head comprises a first three-dimensional model of the set of left semi-circular canals, and a second three-dimensional model of the set of right semi-circular canals; and wherein the processor is configured to (1) provide a two-dimensional projection of the first three-dimensional model, the second three-dimensional model, or both, and (2) to change a color of at least a part of the two-dimensional projection in response to a derived vestibular activity.

9. The system according to claim 1, wherein the processor is configured for deriving vestibular activity from the additional sensor data regarding the eye movement provided by the second sensor device.

10. The system according to claim 1, wherein the processor is configured to generate feedback signal based on the sensor data from the first sensor device, and the additional sensor data from the second sensor device.

11. The system according to claim 1, wherein the first reference indicator and the orientation indicator are configured to guide a physician to position the person's head during the maneuvering scheme.

12. The system according to claim 1, wherein the orientation indicator is designed to light up or change color if the orientation indicator is veering off track during the maneuvering scheme.

13. The system according to claim 1, wherein the orientation indicator moves about in a main window of the graphical display when the head of the person being examined moves and represents the gaze direction of the person.

* * * * *